US012575492B2

(12) United States Patent
Patil et al.

(10) Patent No.: US 12,575,492 B2
(45) Date of Patent: Mar. 17, 2026

(54) CROP MOISTURE DETECTION IN A COMBINE HARVESTER

(71) Applicant: DEERE & COMPANY, Moline, IL (US)

(72) Inventors: Yogesh S. Patil, Jalgaon (IN);
Nandulal Gavali, Pimpri (IN);
Chandrashekhar Bapat, Pune (IN);
Sourabha S. Gokhale, Ichalkaranji (IN)

(73) Assignee: Deere & Company, Moline, IL (US)

( * ) Notice: Subject to any disclaimer, the term of this patent is extended or adjusted under 35 U.S.C. 154(b) by 999 days.

(21) Appl. No.: 17/725,043

(22) Filed: Apr. 20, 2022

(65) Prior Publication Data

US 2023/0337579 A1     Oct. 26, 2023

(51) Int. Cl.
*A01D 41/127*     (2006.01)
*G01N 33/00*     (2006.01)
(Continued)

(52) U.S. Cl.
CPC ....... *A01D 41/127* (2013.01); *G01N 33/0098*
(2013.01); *A01F 12/10* (2013.01);
(Continued)

(58) Field of Classification Search
CPC .............. A01D 41/127; A01D 41/1271; A01D
41/1274; A01D 41/1277; A01F 12/10;
(Continued)

(56) References Cited

U.S. PATENT DOCUMENTS 4,450,671 A     5/1984  Love
6,487,836 B1    12/2002 Coers et al.
(Continued)

FOREIGN PATENT DOCUMENTS

DE     69911302 T2    4/2004
EP     0960557 A1    12/1999
(Continued)

OTHER PUBLICATIONS

Sensor Solutions; TE Connectivity; HS1101LF Relative Humidity Sensor; Date Sep. 2015; pp. 1-6.
(Continued)

*Primary Examiner* — Joseph M Rocca
*Assistant Examiner* — Robert E Pezzuto
(74) *Attorney, Agent, or Firm* — Taft Stettinius & Hollister LLP; Stephen F. Rost

(57)     ABSTRACT
A combine harvester for harvesting crop including a header, to cut crop, and a feeder house having an inlet, connected to the header, and an outlet, wherein the feeder house defines an interior and an exterior located outside the feeder house. The combine harvester includes one or more sensor assemblies connected to the feeder house, wherein each of the sensor assemblies provides a relative humidity value or both of a relative humidity value and a temperature value. A controller is operatively connected to the plurality of sensor assemblies, wherein the controller receives the relative humidity value or temperature value from each of the plurality of sensor assemblies. In response to the received relative humidity value or temperature value, the controller identifies a recommended setting for one or more harvester devices, parts, or components, to avoid grain loss and grain breakage resulting from crop moisture conditions.

20 Claims, 8 Drawing Sheets

(51) Int. Cl.

| | |
|---|---|
| *A01F 12/10* | (2006.01) |
| *A01F 12/18* | (2006.01) |
| *A01F 12/28* | (2006.01) |
| *A01F 12/44* | (2006.01) |

(52) U.S. Cl.
CPC ............. *A01F 12/181* (2013.01); *A01F 12/28* (2013.01); *A01F 12/444* (2013.01)

(58) Field of Classification Search
CPC ...... A01F 12/181; A01F 12/28; A01F 12/444; A01F 12/46; G01N 33/0098; A01B 79/005
See application file for complete search history.

(56) References Cited

U.S. PATENT DOCUMENTS

| | | | | |
|---|---|---|---|---|
| 6,951,514 | B1 * | 10/2005 | Coers | ................... A01D 41/127 460/1 |
| 9,511,646 | B2 * | 12/2016 | Müller | ................... G01N 19/10 |
| 9,826,682 | B2 * | 11/2017 | Blank | ................... A01D 41/127 |
| 10,561,069 | B2 | 2/2020 | Thomas et al. | |
| 2014/0277960 | A1 | 9/2014 | Blank et al. | |
| 2015/0233855 | A1 | 8/2015 | Delie et al. | |
| 2015/0245560 | A1 | 9/2015 | Middelberg et al. | |
| 2019/0246561 | A1 * | 8/2019 | Neitemeier | .......... A01D 41/127 |
| 2020/0217263 | A1 | 7/2020 | Park et al. | |
| 2020/0394580 | A1 | 12/2020 | Bull et al. | |
| 2021/0144919 | A1 | 5/2021 | Romoser | |

FOREIGN PATENT DOCUMENTS

| | | | |
|---|---|---|---|
| EP | 1243174 | A1 | 9/2002 |
| EP | 1266558 | A2 | 12/2002 |
| EP | 1576869 | B1 | 4/2011 |
| EP | 3459337 | A1 | 3/2019 |

OTHER PUBLICATIONS

Snapeda; Humidity Sensors; Website: http://ht.ly/sBsK30gyBp7; "The top 10 humidity sensors"; Dated: Nov. 9, 2017.

Sensirion AG; Environmental Sensors and Humidity Sensors; Website: https://sensirion.com; publicly available as early as Apr. 20, 2022.

TE Connectivity (TE); Temperature and Humidity Sensors; Website: https://www.te.com/global-en/products/sensors/humidity-sensors/humidity-sensor-components.html?tab=pgp-story; publicly available as early as Apr. 20, 2022.

* cited by examiner

CROP MOISTURE DETECTION IN A COMBINE HARVESTER

FIELD OF THE DISCLOSURE

The present disclosure relates to an agricultural vehicle, and more particularly, to a crop combine harvester having a system for moisture detection of the crop being harvested.

BACKGROUND

Agricultural equipment, such as a tractor-drawn combine harvester or a self-propelled combine harvester, includes mechanical systems, electrical systems, hydraulic systems, and electro-hydraulic systems.

One type of agricultural harvester includes the self-propelled combine harvester, having different sections for cutting crop and moving the crop through the harvester. A header for an agricultural combine harvester is arranged to be moved in a forward direction over a field. The header comprises a laterally extending frame supporting a laterally extending cutter bar. Draper conveyers, located at the header, include a draper belt having a feeding direction from outer ends towards a center of the header. A central conveyor, also called a center draper belt conveyor, is disposed between the inner ends of the left and right draper belt conveyors to receive cut crop material and to convey it rearward through a central aperture. The central aperture directs harvested grain, for instance to a thresher where the grain is separated from the plant stalk and delivered to an onboard storage unit. When the onboard storage unit is full, the grain is unloaded to a wagon or tank.

Another type of harvester is configured to harvest corn. The corn harvester includes a corn header having a plurality of cones separated by channels that receive stalks of corn. The channels direct the stalks of corn to a gathering chain that strips the heads of corn from the stalks, which fall to the ground. The heads of corn are directed to a central aperture and the kernels of corn, which are removed from the corn head, are stored in an onboard storage unit for later unloading from the harvester.

The self-propelled grain harvester includes an operator's station where an operator is located to operate and/or monitor the operation of combine harvester. The station includes operator controls, often including a display, to provide the operator with harvester status as well as to provide operator controls for adjusting operating conditions of the harvester.

During the harvesting of crop with a combine harvester, high crop moisture affects overall harvester productivity. Many different types of crop are affected by high relative humidity including, but not limited to, wheat, rye, paddy (rice with husk), and corn. Moisture affects the overall capacity and/or productivity of the combine harvester. For instance in case of high moisture content (e.g 18-20% in paddy or 30-35% in corn), the combine harvester needs to run slowly in order to reduce the grain losses as well as to reduce grain breakage. Under some conditions, the operator runs the combine harvester machine forward at a slow speed to reduce grain losses. In addition, the operator may adjust machine settings in order to avoid grain loss and grain breakage in high crop moisture condition. In some known combine harvesters, control settings determined by an operator are completely based on judgment or are based on a manual procedure to analyze the crop moisture content. These operations can be a tiresome and/or time consuming process since the operator needs to adjust the machine settings until a proper setting is determined in order to achieve optimum performance from the combine harvester based on the crop moisture condition.

What is needed therefore is system and method to adjust the various machine settings of a combine harvester to improve harvesting productivity.

SUMMARY

In one embodiment, there is provided a system for adjusting combine harvester machine settings based on a moisture content of a crop harvested by a combine harvester. The system includes an enclosure having an inlet, an outlet, and a support located between the inlet and the outlet, wherein the inlet receives cut crop. A crop transfer device is disposed within the enclosure to move cut crop through the enclosure from the inlet to the outlet. A sensor assembly is connected to the support, wherein the sensor assembly provides a sensor output of one of or both of a relative humidity value and a temperature value. A controller is operatively connected to the sensor assembly, wherein the controller receives one of or both of the relative humidity value and the temperature value from the sensor assembly.

In some embodiments, the system further includes wherein the enclosure includes a top wall, a bottom wall, and at least one side wall, wherein one of the top wall, the bottom wall, or the at least one side wall supports the sensor assembly.

In some embodiments, the system further includes wherein the enclosure is a feeder house of the combine harvester.

In some embodiments, the system further includes wherein the enclosure defines an external environment located outside the enclosure and an internal space located inside the enclosure, and the sensor assembly includes a first aperture exposed to the external environment and a second aperture exposed to the internal space.

In some embodiments, the system further includes wherein the sensor assembly includes a first sensor and a second sensor, wherein the first sensor is supported an internal support of the sensor assembly to be exposed to the external space through the first aperture and the second sensor is supported by the sensor assembly to be exposed to the internal space through the second aperture.

In some embodiments, the system further includes wherein the sensor assembly includes a sidewall, a top cover and a bottom cover each coupled to the sidewall, wherein the top cover defines the first aperture and the bottom cover defines the second aperture, and the internal support is located between the top cover and the bottom cover.

In some embodiments, the system further includes wherein each of the first aperture and the second aperture include one of a mesh structure, a grate structure, or a perforated structure.

In some embodiments, the system further includes wherein the controller includes a processor and a memory, wherein the memory is configured to store program instructions and the processor is configured to execute the stored program instructions to determine one or more machine settings based on one or more outputs of the sensor assembly including: a threshing speed of the combine harvester; a concave clearance of a concave of the combine harvester; a fan speed of a fan of the combine harvester; and a forward speed of the combine harvester.

In some embodiments, the system further includes a user interface operatively connected to the controller, wherein the user interface includes a display screen to display moisture content information of the crop based on one of or both of the relative humidity value and the temperature value.

In some embodiments, the system further includes wherein the processor is configured to execute the stored program instructions to provide adjustment indicators for adjusting one or more of the threshing speed, the concave clearance of the concave, speed of the fan, and the forward speed of the combine harvester when the relative humidity value exceeds a predetermined relative humidity value or the temperature value exceeds a predetermined temperature value.

In some embodiments, the system further includes wherein the processor is configured to execute the stored program instructions to automatically adjust one or more of the threshing speed, the concave clearance of the concave, speed of the fan, and the forward speed of the combine harvester when the relative humidity value exceeds a predetermined relative humidity value or the temperature value exceeds a predetermined temperature value.

In another embodiment, a combine harvester for harvesting crop includes a header to cut crop and a feeder house including an inlet, connected to the header, and an outlet. The feeder house defines an interior and an exterior located outside the feeder house. A drum and a concave are disposed within the feeder house wherein the concave is disposed adjacently to the drum. A threshing unit is operatively connected to the outlet of the feeder house. A plurality of sensor assemblies is connected to the feeder house, wherein each of the plurality of sensor assemblies includes one or more sensors providing a relative humidity value or both of a relative humidity value and a temperature value. A controller is operatively connected to the plurality of sensor assemblies, wherein the controller receives the relative humidity value and the temperature value from each of the plurality of sensor assemblies.

In some embodiments, the combine harvester includes wherein each of the plurality of sensor assemblies includes a first sensor and a second sensor, wherein the first sensor is supported by an internal support of the sensor assembly to be exposed to an external environment through the first aperture and the second sensor is supported by the sensor assembly to be exposed to an internal space through the second aperture.

In some embodiments, the combine harvester includes wherein each of the first sensor and the second sensor includes a semiconductor polymer sensor.

In some embodiments, the combine harvester includes wherein the sensor assembly includes a sidewall, and a top cover and a bottom cover, each coupled to the sidewall, wherein the top cover defines the first aperture and the bottom cover defines the second aperture, and the internal support is located between the top cover and the bottom cover.

In some embodiments, the combine harvester includes wherein each of the first aperture and the second aperture include one of a mesh structure, a grate structure, or a perforated structure.

In some embodiments, the combine harvester includes wherein the controller includes a processer and a memory. The memory is configured to store program instructions and the processor is configured to execute the stored program instructions to adjust one or more of: a threshing speed of the combine harvester; a concave clearance of a concave of the combine harvester; a fan speed of a fan of the combine harvester; and a forward speed of the combine harvester.

In an additional embodiment, there is provided a method of modifying the operation of a combine harvester while harvesting crop from a field. The method includes: threshing cut crop as the combine harvester moves through the field; identifying a relative humidity value or both of a relative humidity value and temperature value in both an interior and an exterior of a feeder house of the combine harvester; adjusting one or more of a plurality of machine operation including: i) a threshing speed of the combine harvester; ii) a concave clearance of a concave of the combine harvester; iii) a fan speed of a fan of the combine harvester; and iv) a forward speed of the combine harvester based on the determined relative humidity value or both of the relative humidity value and temperature value in the feeder house.

In some embodiments, the method includes wherein the adjusting step includes adjusting one or more of the plurality of machine settings in response to one of: i) a user input received from a user interface or ii) automatically based on an instruction from a controller processor.

In some embodiments, the method includes wherein the identifying step includes identifying the relative humidity value or both of the relative humidity value and the temperature value in the interior and the exterior of the feeder house with a sensor assembly having a first sensor directed to the exterior of the feeder house and a second sensor directed to the interior of the feeder house.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein.

Corresponding reference numerals are used to indicate corresponding parts throughout the several views.

DETAILED DESCRIPTION

Figure 1:
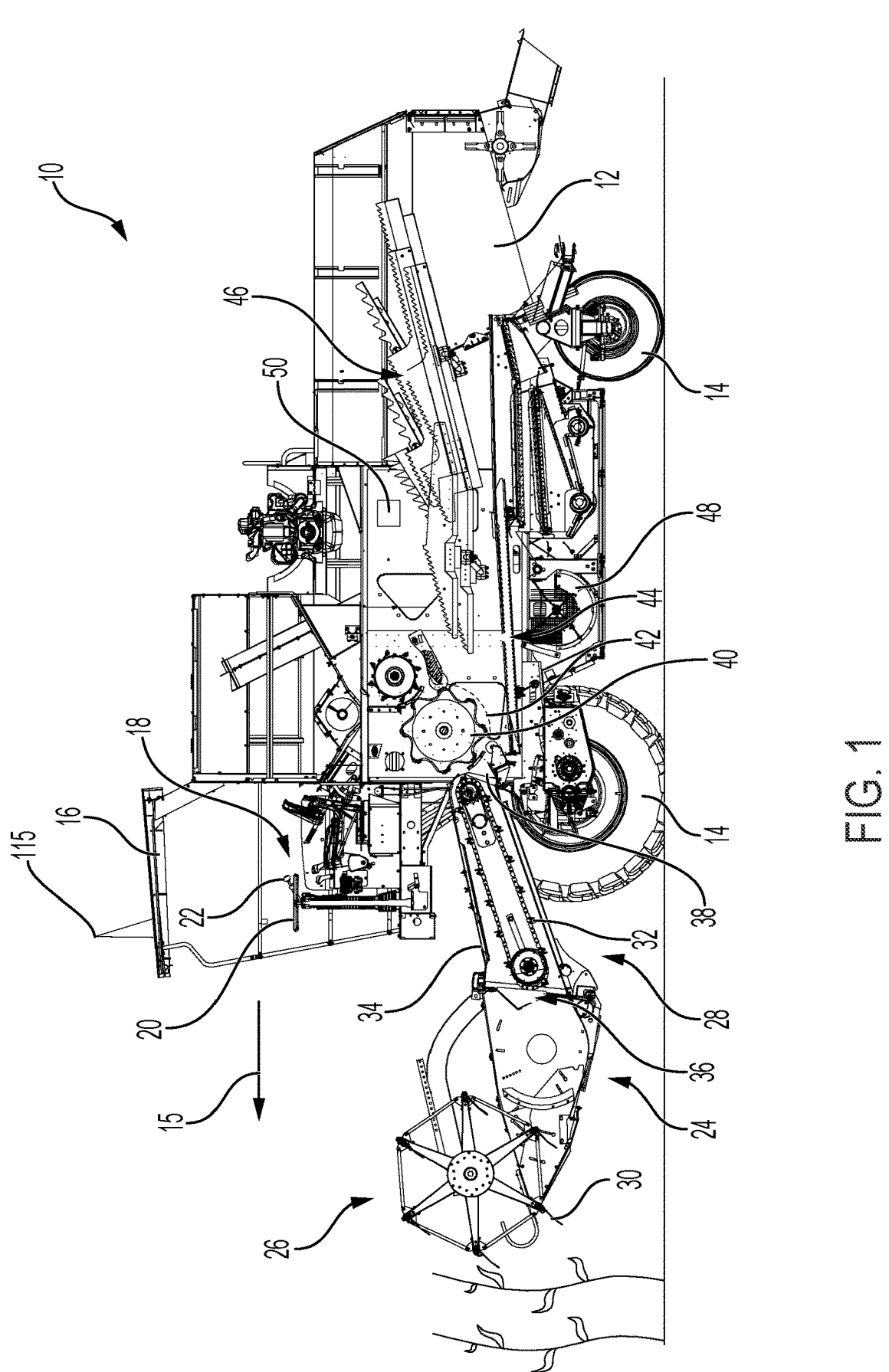
FIG. 1 is a partially sectioned elevational side view of an agricultural combine harvester.

For the purposes of promoting an understanding of the principles of the present disclosure, reference will now be made to the embodiments described herein and illustrated in the drawings and specific language will be used to describe the same. It will nevertheless be understood that no limitation of the scope of the present disclosure is thereby intended, such alterations and further modifications in the illustrated devices and methods, and such further applications of the principles of the present disclosure as illustrated therein being contemplated as would normally occur to one skilled in the art to which the present disclosure relates.

FIG. 1 illustrates one embodiment of an agricultural combine harvester 10 including a chassis 12 with wheels 14 in contact with the ground. Wheels 14 are coupled to the chassis 12 and are used for propulsion of the combine 10 in a forward operating or travelling direction 15. Surface engaging members, other than wheels, are contemplated, such as treads. The operation of the combine 10 is controlled from an operator's station 16. The operator's station 16, in different embodiments, includes one or more controls located at an operator input device 18 for controlling the operation of the harvester 10. The operator input device 18 includes a steering wheel 20 and a throttle 22. A draper header 24 is disposed at a forward end of the harvester 10 and includes a cutting knife or cutterbar (not shown) to cut crop being harvested. The cut crop includes any variety and types of different crops including wheat, soybeans, sorghum, barley, paddy, and other grains. At substantially the same time the grain is cut, a pickup reel assembly 26, rotates as understood by those skilled in the art, to move or force the cut crop toward a crop transfer device 28, such as a slope conveyor 28. The pickup reel assembly 26 includes a plurality of fingers 30. The fingers 30 lift and move the cut crop over the cutterbar, as well as to comb through the cut crop to provide a degree of separation of the crop. The slope conveyer includes a conveyor belt 32 which is located within a feeder house 34 having an inlet 36 and an outlet 38. The conveyor belt 32 rotates in a clockwise direction as illustrated to move cut crop from the inlet 36 to the outlet 38.

The cut crop is moved along a length of the feeder house 34 from the inlet 36 to the outlet 38 where the cut crop is delivered to a threshing cylinder 40 disposed adjacently to a concave 42. As the threshing cylinder 40 rotates in a clockwise direction as illustrated, the cut crop moves between the rotating threshing cylinder 40 and the concave 42 to provide an initial threshing of the cut crop. A distance between the threshing cylinder 40 and the concave 42 is adjustable to separate grain from stems. Grain, that is part of the threshed cut crop, is separated from the stems of the cut crop and moves from the concave 42 to a threshing screen 44 that is part of a crop processing arrangement 46, as is understood by those skilled in the art. A blower fan 48, also part of the crop processing arrangement 46, is located beneath the threshing screen 44 to provide a grain cleaning function to separate the grain, i.e. kernels, from the stems and other cut crop parts including a sheath as in the case when wheat is the cut crop.

A harvester controller 50 is supported by the chassis 12 and is connected to, or is a part of, a CAN (controller area network) bus as is known by those skilled in the art. The harvester controller 50, in different embodiments, is located at various locations within the harvester 10 and the location shown in FIG. 1 is merely representative.

Figures 2, 3:
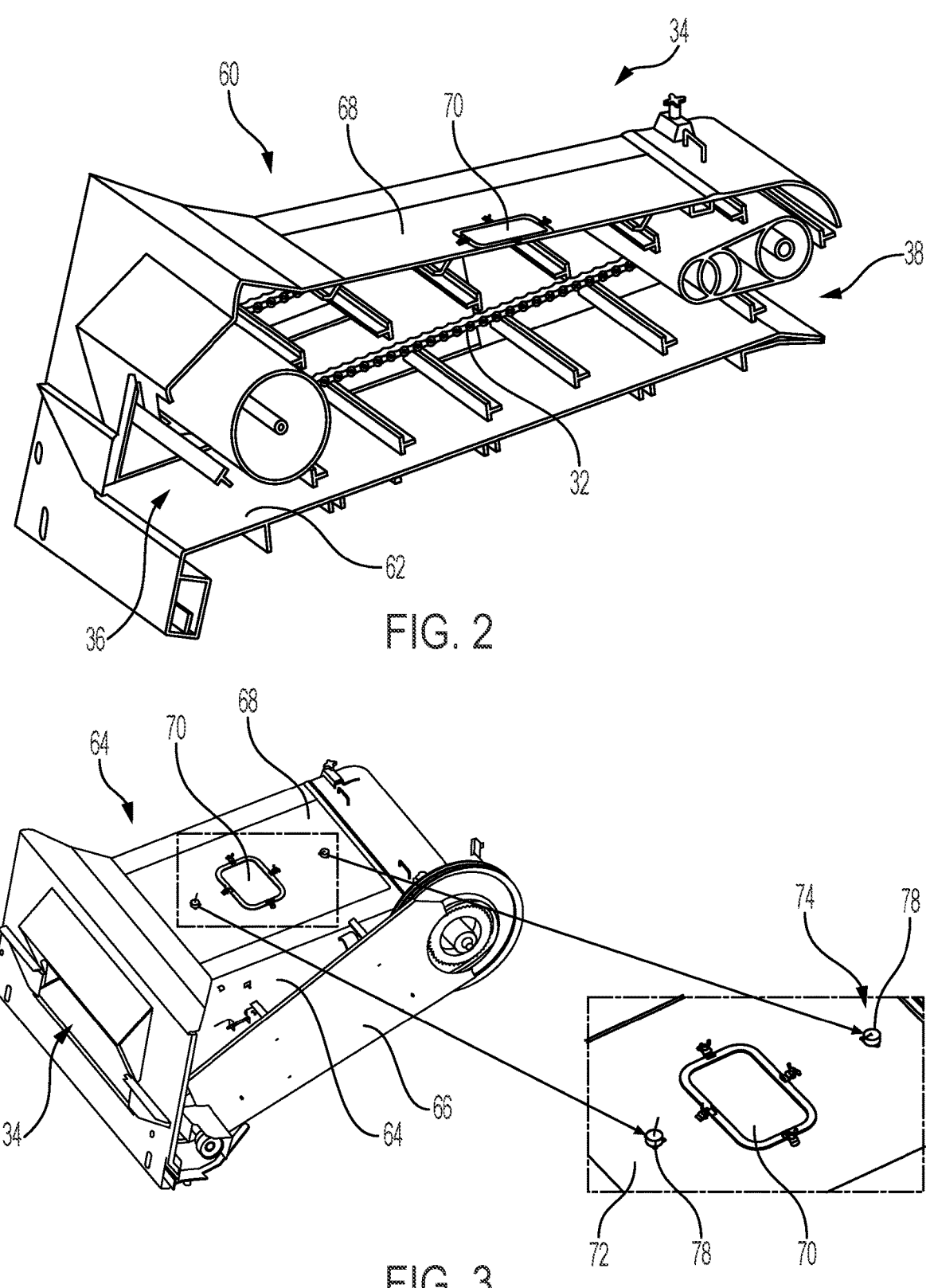
FIG. 2 is a sectioned elevational perspective view of a feeder house of an agricultural combine harvester.
FIG. 3 illustrates a perspective view of a feeder house of an agricultural combine harvester.

FIG. 2 is a sectioned elevational perspective view of the feeder house 34 and FIG. 3 illustrates a perspective view of the feeder house 34. As seen in FIGS. 2 and 3, the feeder house 34 includes a top wall 60, and a bottom wall 62, each of which extend between the inlet and the outlet 38. Side walls 64 are coupled to the top and bottom walls 60 and 62 to complete the feeder house 34 in which the conveyor belt 32 is located. A drive mechanism 66 coupled to the feeder house 34 is configured to drive the conveyor belt 32 to move cut crop from the inlet 36 to the outlet 38.

Figure 4A:
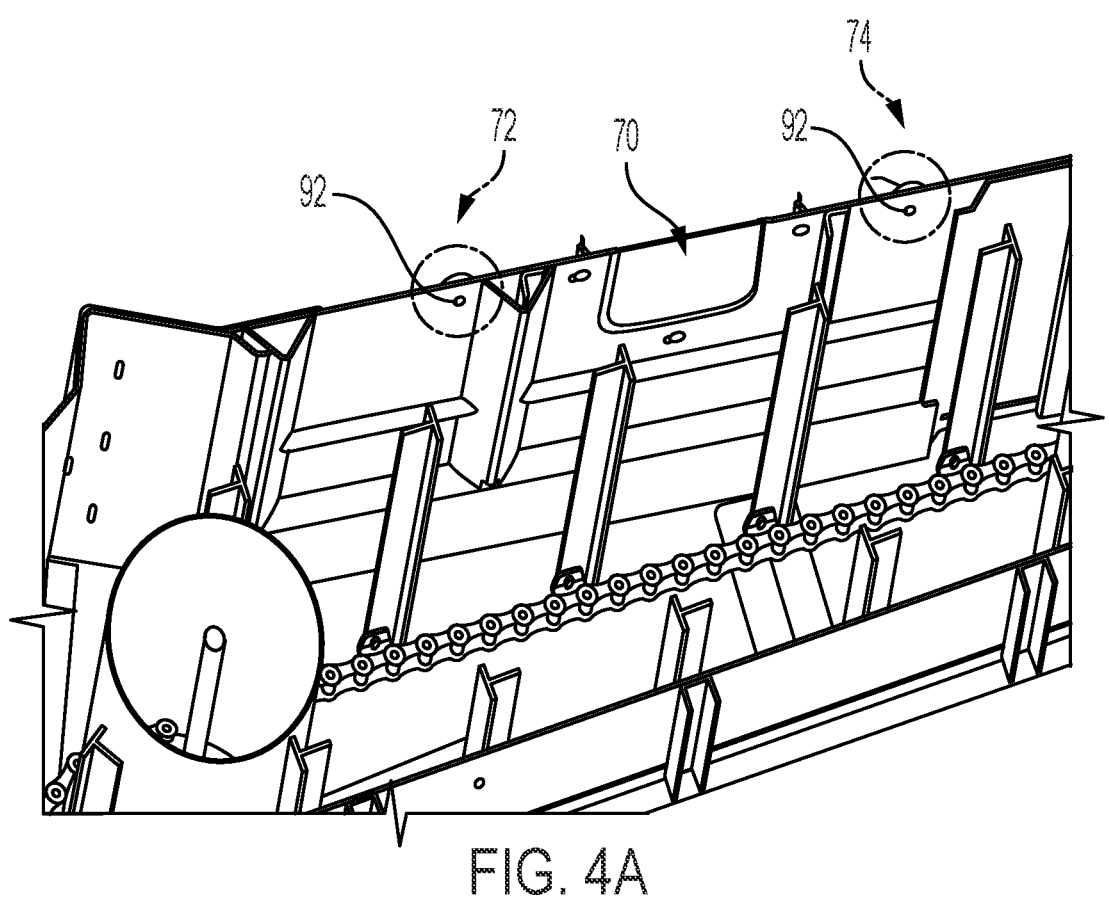
FIGS. 4A and 4B illustrate an internal view of a feeder house of an agricultural combine harvester including a breakout view illustrating a sensor assembly.
Figure 6:
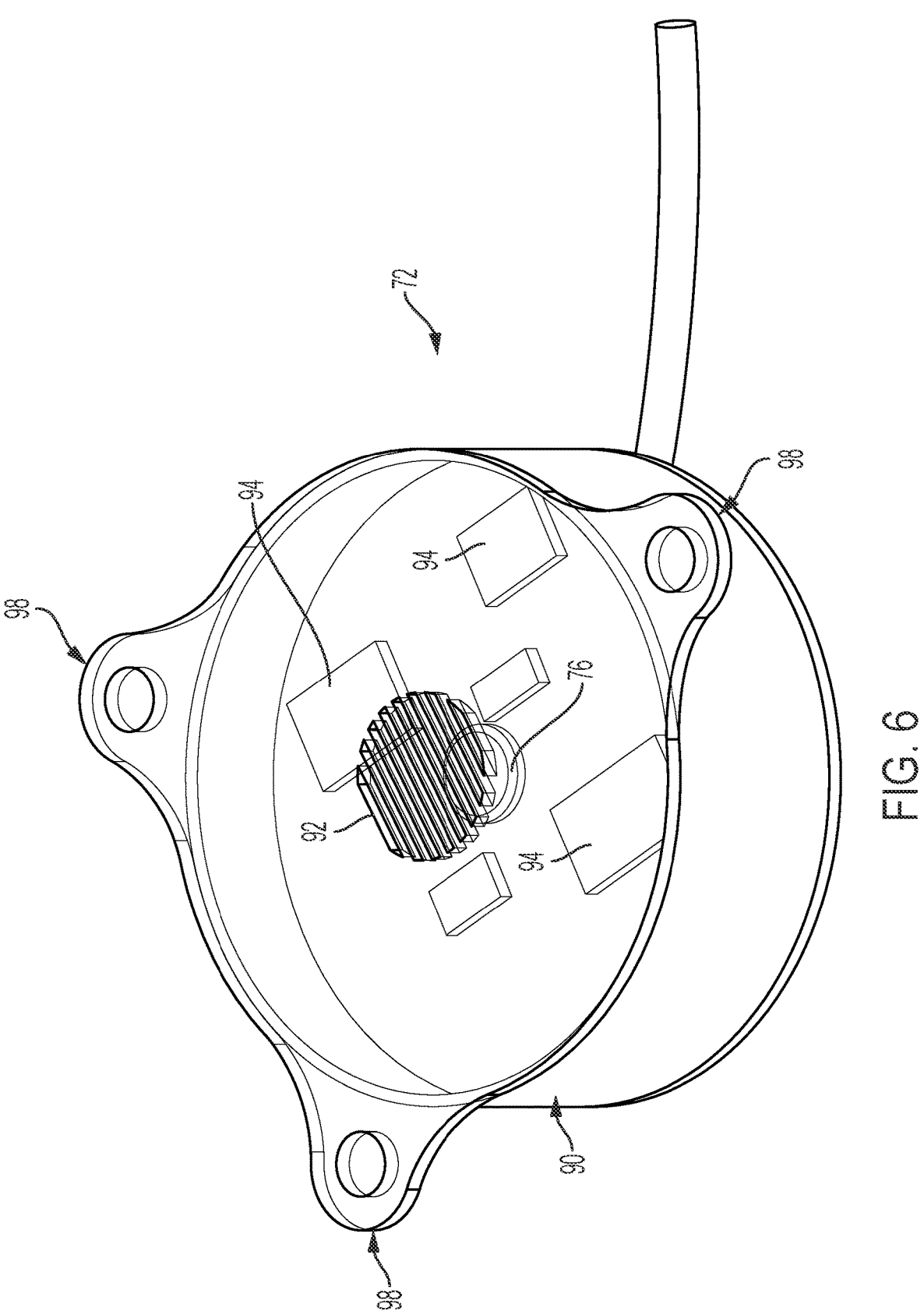
FIG. 6 illustrates a bottom view of a sensor assembly.
Figures 7, 8:
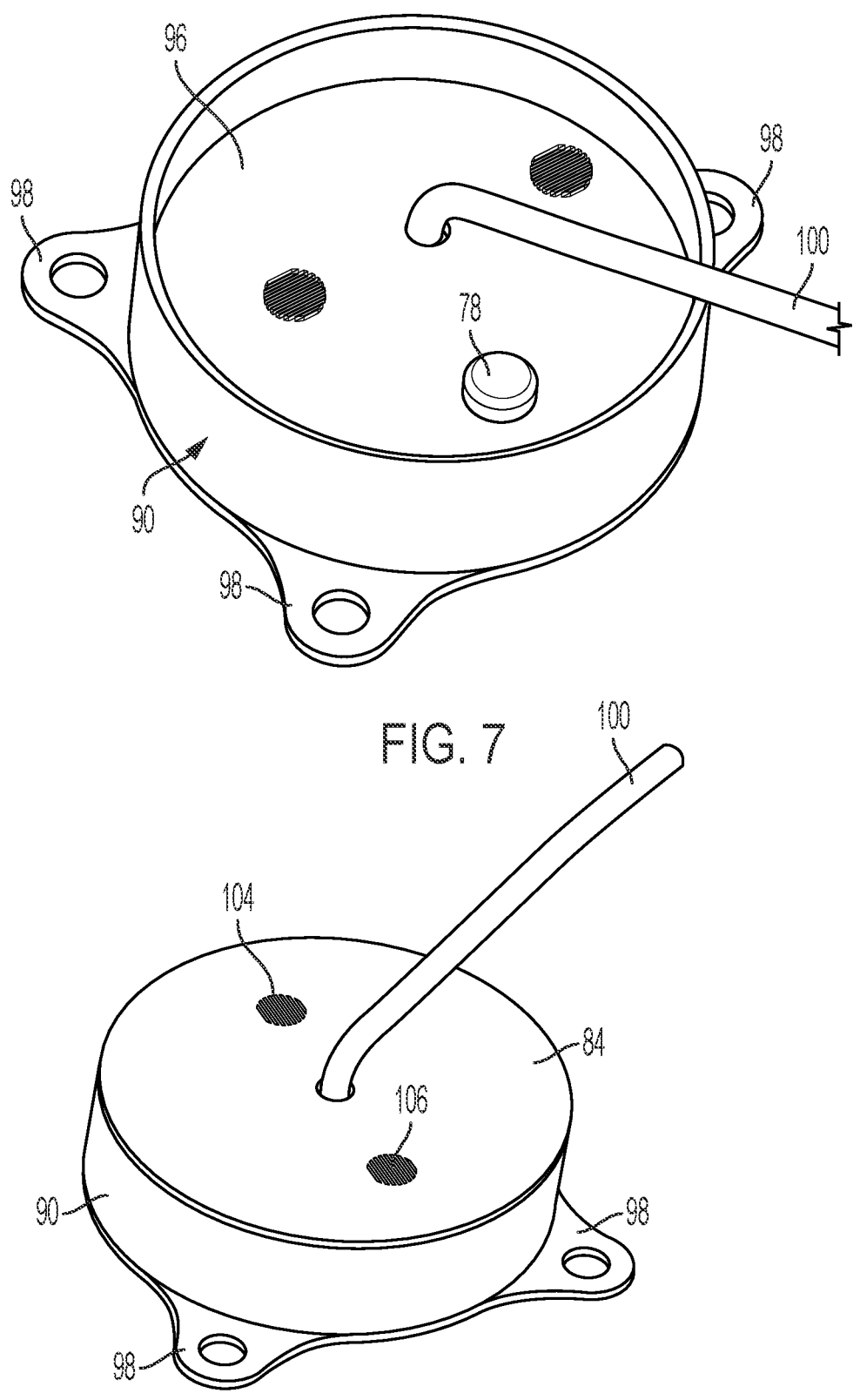
FIG. 7 illustrates a top view of a sensor assembly without a top cover with a top cover made transparent to illustrate inside parts.
FIG. 8 illustrates a top view of a sensor assembly with a top cover.

The top wall 60, in one embodiment, includes a support 68, such as a panel, configured to support a door 70. On either side of the door 70 is a first sensor assembly 72 and a second sensor assembly 74, each of which are removably coupled to the panel 68. The door 70 is removable and enables access to each of the first sensor assembly 72 and the second sensor assembly 74 for installation, replacement, or repair. Each of the sensor assemblies 72 and 74 include, in at least one embodiment, a first sensor 76, as illustrated in FIG. 6, and a second sensor 78, as illustrated in FIG. 7. The first sensor 76 of each sensor assembly 72 and 74 is directed to and exposed to an internal environment inside the feeder house 34 as illustrated in FIG. 4A. The second sensor 78 is directed to and exposed to the external environment of combine harvester 10 as seen in FIG. 3.

Figure 4B:
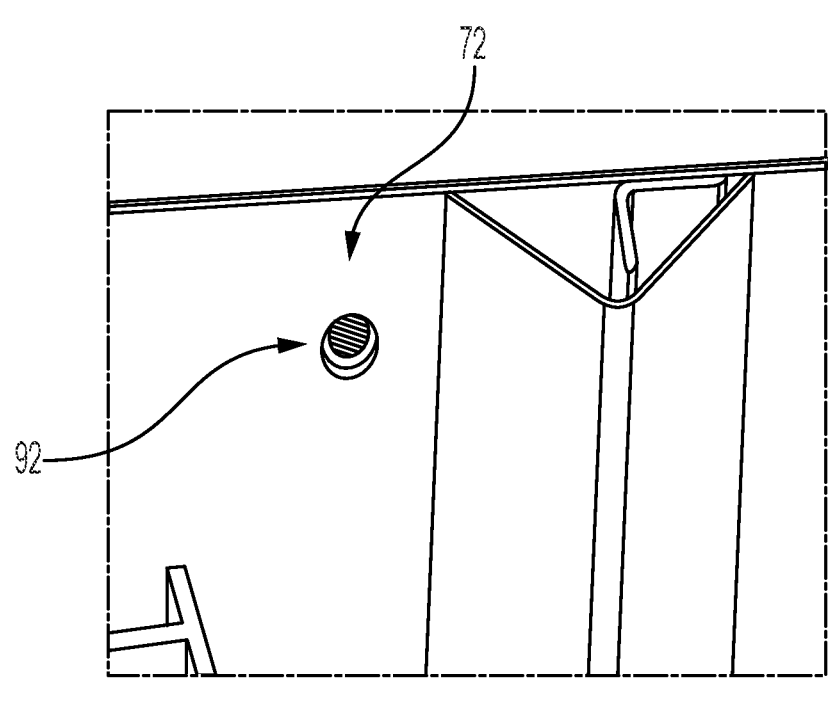

As seen in FIGS. 3 and 4, the sensor assembly 72 includes both sensors 76 and 78 and the sensor assembly 74 includes both sensors 76 and 78. In one embodiment, each of the sensors 76 and 78 are sensors that measure both relative humidity and temperature. For instance, the sensor assembly 72 measures both relative humidity and temperature of the ambient air external to the feeder house 34 using sensor 78 and measures both relative humidity and temperature of the air within the enclosure feeder house using sensor 76. Likewise, sensor assembly 74 use sensors 78 for ambient air and sensor 76 for air within the feeder house 34. As seen in FIG. 4B, sensor assembly 72, which is mounted to the panel 68, includes the sensor 76 which is directed to the internal environment of the feederhouse 34.

Each of the sensor assemblies 72 and 74 includes both the sensor 76 and the sensor 78 as well as a processor, that is connected to each of the sensors 76 and 78. The sensors 76, 78, and the processor are contained within a sensor housing 80. The processor is common between sensor 76 and 78. This mean both sensors 76 and 78 are connected to a single processor. In other embodiments, each sensor is coupled to its own processor. Each of the two sensors 76 and 78 are physically, i.e. environmentally isolated, meaning that sensor 76 has access to air and temperature inside feeder house and sensor 78 has access to outside environment. Both sensors 76 and 78 measure relative humidity as well as temperature. The sensor assemblies 72 and 74 are each considered to be a dual sensor in that both sensor elements 76 and 78 are part of one sensor assembly. The sensor assembly is capable of calculating relative humidity based on predictive control implemented inside the processor located on the sensor assembly.

As described herein, predictive control is a continuous running algorithm in a processor. Predictive control uses current or instantaneous data measured by the sensor elements to predict an accurate physical entity of interest, which as described herein is relative humidity. To perform this analysis, the algorithm uses multiple inputs e.g. 1) calibration data logged in a controller during factory release of vehicle, 2) calibration data run after the factory release to re-calibrate the sensor elements, 3) current state of the vehicle, 4) crop configuration settings if available, which are available mostly for high end models, and 5) most importantly outside the feeder house relative humidity and temperature measurements along with inside feeder house measurements. Based on these inputs, the processor reduces or eliminates any noise and any ambiguity in measurement and generate appropriate action.

Figure 5:
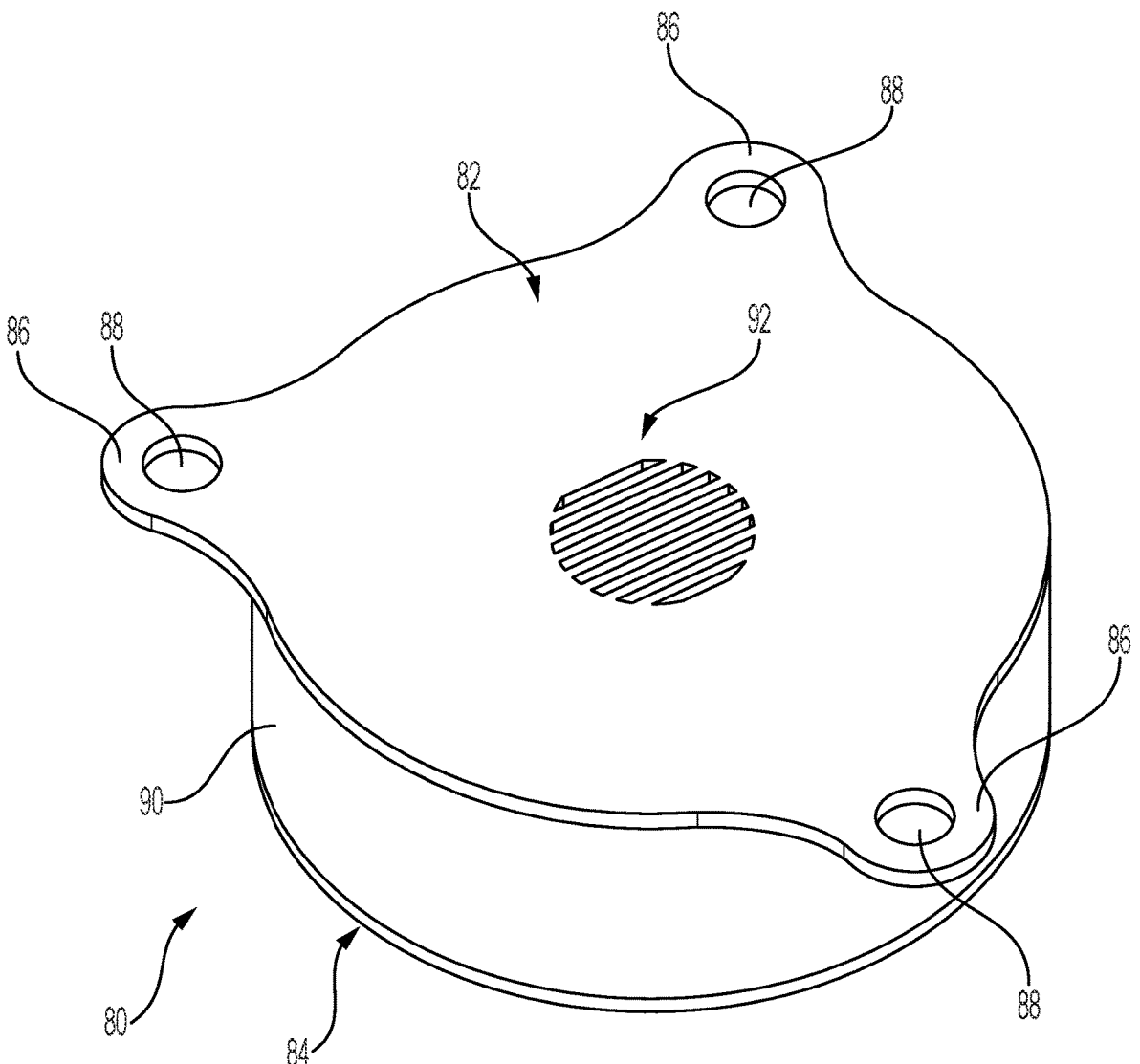
FIG. 5 illustrates a bottom view of a sensor assembly with a bottom cover made transparent to illustrate inside parts.

FIG. 5 illustrates a bottom side perspective view one embodiment of the sensor assembly 72, whose description applies to sensor assembly 74. The sensor assembly 72 includes the sensor housing 80 having a bottom cover 82 and a top cover 84. The bottom cover 82 is generally circular and includes ears or tabs 86 each of which includes mounting holes 88. A cylindrical sidewall 90 is located between and connected to each of the bottom cover 82 and the top cover 84. The panel 68 of the housing includes cutouts of a sufficient size to receive the circumference of the sensor assemblies 72 and 74 which are connected to the panel 68 with connectors extending through the panel 68. When connected, bottom cover 82 is placed in contact with the panel 68 and attached thereto with connectors extending through the mounting holes 88 and into the panel 68. The top cover 84 is left exposed to the ambient air.

As seen in FIGS. 5 and 6, the bottom cover 82 includes a mesh aperture 92 that is collocated with an aperture (not shown) in the panel 68. FIG. 6 illustrates only the mesh aperture 92 and not the rest of cover 82 to show components within the sensor assembly. Consequently, the air located within the feeder house 34 is directed through the aperture in the panel 68 to the sensor 76 through mesh aperture 92. Additional electrical components 94 are supported on an internal support 96, i.e. a printed circuit board, supported within the sensor housing 80. In at least one embodiment, one of the components 94 is a processor and is connected to the sensors 76 and 78. The electrical components 94 include, but are not limited to, discrete electrical devices and/or integrated circuit devices coupled to the sensors which process or transmit sensor information to a control system as described herein. In the embodiment of FIG. 6, the sidewall 90 includes sidewall tabs 98 configured to be joined with tabs 86 of the bottom cover 82. In other embodiments, the apertures include but are not limited to a mesh structure, a grate structure, or a perforated structure.

FIGS. 7 and 8 illustrate a top perspective view of the sensor assembly 72 illustrating the internal support 96 that supports the sensor 78. A wiring harness 100 extends to and through the internal support 96 and is electrically connected to the electrical components 94, as seen in FIG. 6, as well as to sensor 78. The wiring harness 100 is connected to the controller 50. As seen in FIG. 8, the wiring harness 100 extends through the top cover 84 which is coupled to the sidewall 90. The top cover 84 includes a first mesh aperture 104 and a second mesh aperture 106 each of which expose the sensor 78 to air located externally to the housing 60. In one embodiment, each of the apertures 92 of FIG. 6 and apertures 104 and 106 of FIG. 8 include a plurality of adjacently located slots. In other embodiments, the apertures 92, 104 and 106 include other configurations of apertures to permit air to enter the sensor assemblies where the sensors 76 and 78 are located. Each one of the slots is spaced from an adjacent slot to enable air to move to the internally located sensors, while being spaced sufficiently close to prevent unwanted material from entering the housing. See also FIG. 7 where the apertures 104 and 106 are illustrated in phantom illustrated the location of the apertures 104 and 106 in the absence of the top cover 84.

Figure 9:
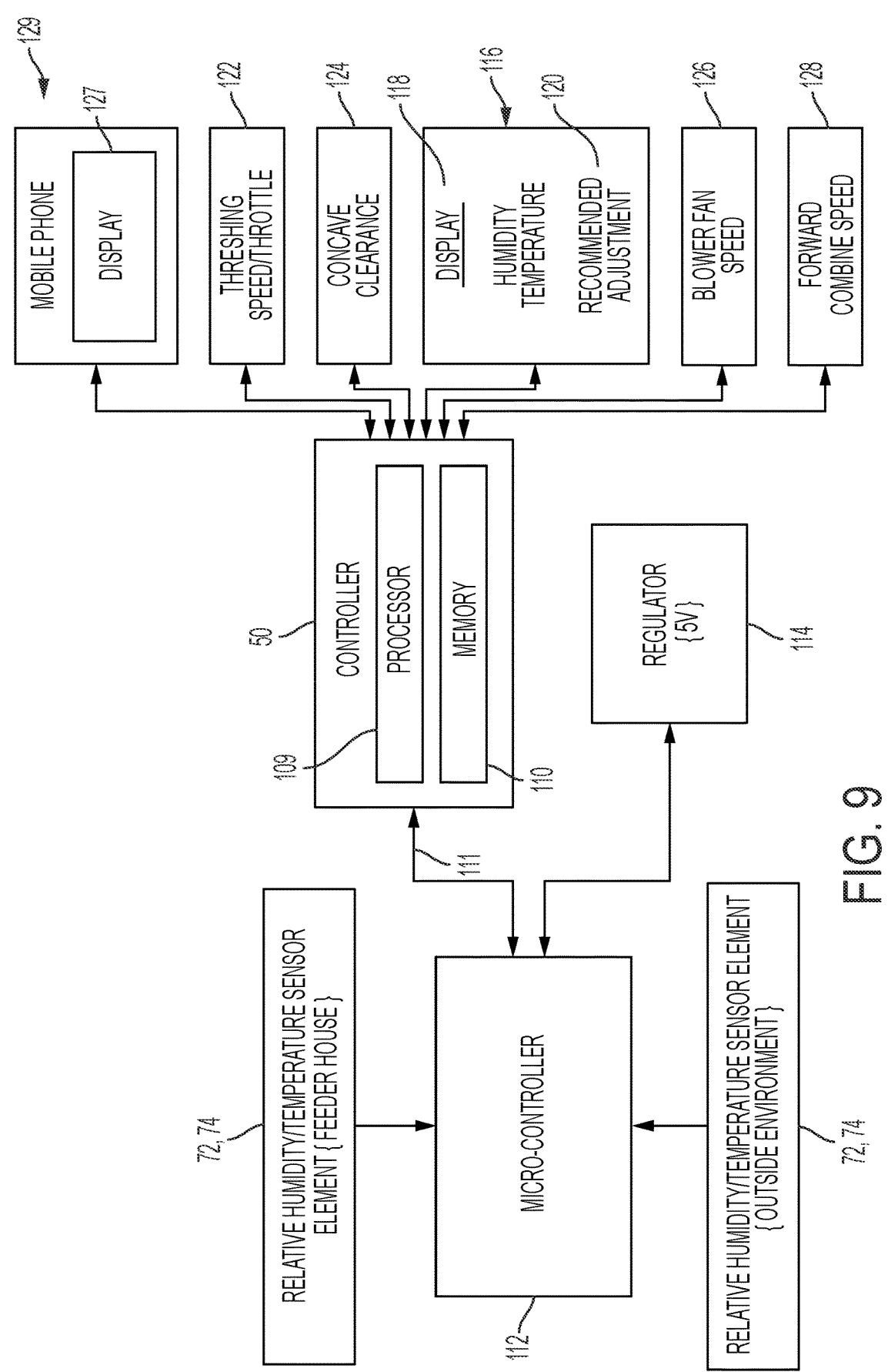
FIG. 9 illustrates a block diagram of a control system for determining crop moisture based on one or both of relative humidity and temperature.

FIG. 9 illustrates a block diagram of the control system 108 for determining crop moisture based on relative humidity or both of relative humidity and temperature. The control system 108 includes the controller 50, which includes, or is coupled to, a processor 109 and a memory 110, as would be understood by one skilled in the art. The controller 50, in different embodiments, is a part of a CAN bus 111, or is separate from, but electrically coupled, to the CAN bus 111. The control system 108 includes the relative humidity/temperature sensor elements of sensor assemblies 72 and 74, which sense temperature and/or relative humidity within the feeder house 34 and outside the feeder house 34. Each of the sensors located within the assemblies 72 and 74 is electrically coupled to a microcontroller 112, which is powered by a five (5) volt regulator 114. The microcontroller 112, in different embodiments, is located at one of the sensor assemblies 72 or 74 or is a part of the controller 50.

In one embodiment, the microcontroller 112 receives temperature data and relative humidity data from each of the assemblies 72 and 74. The temperature data and relative humidity data are received by the processor 109 located in the controller 50 and the processor 109 determines a relative humidity, using both the temperature and relative humidity data, which are used to determine the moisture content of the crop moving within the feeder house 34. By sensing the dual relative humidity/temperature sensing of ambient conditions both inside and outside the feeder house 34, the controller 50, using the processor and memory 110 provides an accurate determination of relative humidity, and therefore moisture content of the grain, that is independent of environmental and weather conditions.

As a result of a real time comparison of ambient air relative humidity and moisture to feeder house data, a prediction algorithm, the controllers 50 and/or controller 112 remove data ambiguity, such as additional moisture accumulated due to prolonged use of machine, humidity change by temperature difference etc. A machine learning or advanced prediction algorithm resident in the controller works on continuous integration of a data set. During tractor calibration, an advanced control algorithm calibrates and stores the respective calibration data. During startup the sensors refreshed with a new calibration to make adjustments for aging, dust and ambient factors. During operation, predictive control continuously integrates the data with different factors such as operating environmental condition, crop type, vehicle speed and time of operation to accurately predict the moisture content and communicate to the controllers 50 and/or controller 112.

The controller 50 and micro-controller 112 leverage machine learning and advanced prediction optimization techniques to reduce or eliminate noisy and erratic data which provides additional accuracy to the received data. By reducing or eliminating noise and erratic data, the determined moisture content is used by the operator to configure the harvester and its environment for stable performance. In one embodiment, the relative humidity/temperature values are saved into a memory of the microcontroller 112. In another embodiment, the relative humidity/temperature values are transmitted by the micro-controller 112 to the controller 50 for storage in memory 110. In another embodiment, the functions of the microcontroller 112 are performed by the controller 50 and a separate microcontroller is not included.

In one embodiment, the relative humidity sensor works on a capacitive principle. A sensor tip of the relative humidity sensor is made of a special polymer material. It is one sensing unit which senses two entities namely, relative humidity and temperature. The sensor is considered to be a smart sensor which uses two such elements, one for the ambient air and one for the feeder house. Both sensing elements are part of one single sensor. In one embodiment, the sensor tip is a semiconductor polymer sensor. The material of the tip changes its capacitance when the sensor experiences relative humidity. The change in capacitance is linearized by the microcontroller 112, or the controller 50, and is converted to a digital value of relative humidity. Once the value of relative humidity is determined the moisture content of the grain is determined.

Once the values of temperature and relative humidity are determined and stored in the memory of the micro-controller 112, the stored data is transmitted to the controller 50 where the controller 50 identifies one or more recommended adjustments to the operating characteristics, i.e. machine settings; of the combine harvester 10. By adjusting the machine settings of devices, components, or parts, the performance of the combine harvester 10 is improved to provide an optimized performance resulting in a harvested grain that includes a moisture content at or near a preferred value of moisture content.

The controller 50, in different embodiments, is a single controller or a plurality of controllers operatively coupled to one another. The controller 50 includes one or both of a hardwired connection or a wireless connection, such that the controller is operatively coupled to other components of the work machine 10. The controller 50, in different embodiments, is operatively coupled to such components via hard-wire connections or wireless connection such as Wi-Fi, Bluetooth, other known means of wireless communication. Thus, in different embodiments the controller 50 is located on the work machine 10 or is located remotely, away from the work machine 10.

The controller 50, in different embodiments, includes a computer, computer system, or other programmable devices. The controller 50 includes one or more processors, including microprocessors, and an associated memory, which can be internal to the processor or external to the processor. The memory can include random access memory (RAM) devices comprising the memory storage, as well as any other types of memory, e.g., cache memories, non-volatile or backup memories, programmable memories, or flash memories, and read-only memories. In addition, the memory can include a memory storage physically located elsewhere from the processing devices and can include any cache memory in a processing device, as well as any storage capacity used as a virtual memory, e.g., as stored on a mass storage device or another computer coupled to controller 50. The mass storage device can include a cache or other dataspace, which can include databases. Memory storage, in other embodiments, is located in the "cloud", where the memory is located at a distant location from the controller 50, which provides the stored information wirelessly to the controller 50 through an antenna 115, typically supported by the operator's station 16 of the vehicle 10. The antenna 115 (see FIG. 1) that receives or transmits information from the distant location with a transmitter/receiver (not shown).

The controller 50 executes or otherwise relies upon computer software applications, components, programs, objects, modules, or data structures, etc. Software routines, resident in the included memory, are executed in response to the signals received from the sensors or through the micro-controller 112. In other embodiments, the computer software applications are located in memory 50 or in the cloud. The executed software includes one or more specific applications, components, programs, objects, modules or sequences of program instructions typically referred to as "program code". The program code includes one or more program instructions located in memory and other storage devices that execute the instructions that are resident in memory, which are responsive to other program instructions or machine settings generated by the system. The processor 109 is configured to execute the stored program instructions.

The controller 50, which includes the processor 109 and the memory 110 in the illustrated embodiment, is configured to receive temperature and/or relative humidity information and to display the information on a user interface device 116, which includes a display 118. In one embodiment, the temperature/relative humidity information is used to derive moisture content of the harvested crop. In addition to the content information being displayed, the display 118 also displays one or more recommended machine adjustments 120, i.e. adjustment indicators, to provide suggested adjustments to one or more machine settings. For instance, the machine settings to be adjusted include, but are not limited to, a threshing speed 122, a thresher concave clearance 124, a blower fan speed 126, and a forward speed 128 of the combine harvester. Consequently, one or more suggested adjustments are displayed for viewing by the operator on the display 118. The controller 50 or micro-controller 112 identifies a recommended setting for one or more harvester devices, parts, or components, to avoid grain loss and grain breakage resulting from crop moisture conditions.

In one or more embodiments, each one of the threshing speed, the blower fan speed, the thresher concave clearance, display a recommended range of settings. In one or more embodiments, each of the settings includes a recommended range of settings. The recommended ranges of settings enables the operator to pick a value located between a low value of the range and a high value of the range. In this way, the operator is not limited to one specific value, but can adjust the value within a suggested range of values based on the operator's experience. For instance, the recommended thresher concave clearance is displayed as a range of values from a lower acceptable value to a higher acceptable value. The operator then selects a desired value within this range by selecting the appropriate desired value, using a slider in one embodiment. In other embodiments, other mechanisms to select the desired value are contemplated included a keyboard to input the desired value. In another embodiment, the controller 50 automatically adjusts the values of each of the ranges. In one or more embodiments, adjustments are manual, automatic, or both depending on the type of harvester machine. A base machine would include, for instance, manual adjustment controls, and a higher end machine would include, for instance, automatic adjustment. Such settings include, but are not limited to, blower fan speed in RPM, combine forward speed in miles per hour (mph) or kilometers per hour (kph), threshing speed in RPM, relative humidity percentage (%), and temperature in degrees C. or degrees F.

Upon display of the recommended range of settings, the operator adjusts the one or more harvester machine settings though the appropriate machine control devices. For instance, if the recommended adjustment indicates that the threshing speed should be adjusted, the threshing speed is adjusted with a throttle 122, or other speed adjusting devices. Other recommended adjustments include a recommended adjustment of one or more of: a clearance of the concave 42 with a concave clearance device 124; a fan speed adjustment of the fan 48 with a fan speed control device 126; an adjustment of the forward speed of the combine harvester 10 with a speed control device 128, such as a throttle.

In one embodiment, the user interface 116, which is coupled to the controller 50, includes displayed control buttons, such as touch screen buttons, which are adjusted in response to the recommended adjustments. In another embodiment, a display 127 of a mobile or cellular phone 129 displays information to the operator. In one embodiment, the display 127 of the cellular phone displays recommended adjustments. In another embodiment, the display of the cellular phone displays control buttons which when selected adjust the throttle 122, the concave clearance 124, the fan speed 126, and the forward speed 128 of the combine 10.

The cellular phone, in different embodiments, includes a software application, i.e. app, which is configured to provide display features and other user input features as described herein. In one or more embodiments, the control system 108 includes one or both of the display 118 and the cellular phone 129 having the display 127. In one or more embodiments, the display 118 and the display 127 display the same information.

Figure 10:
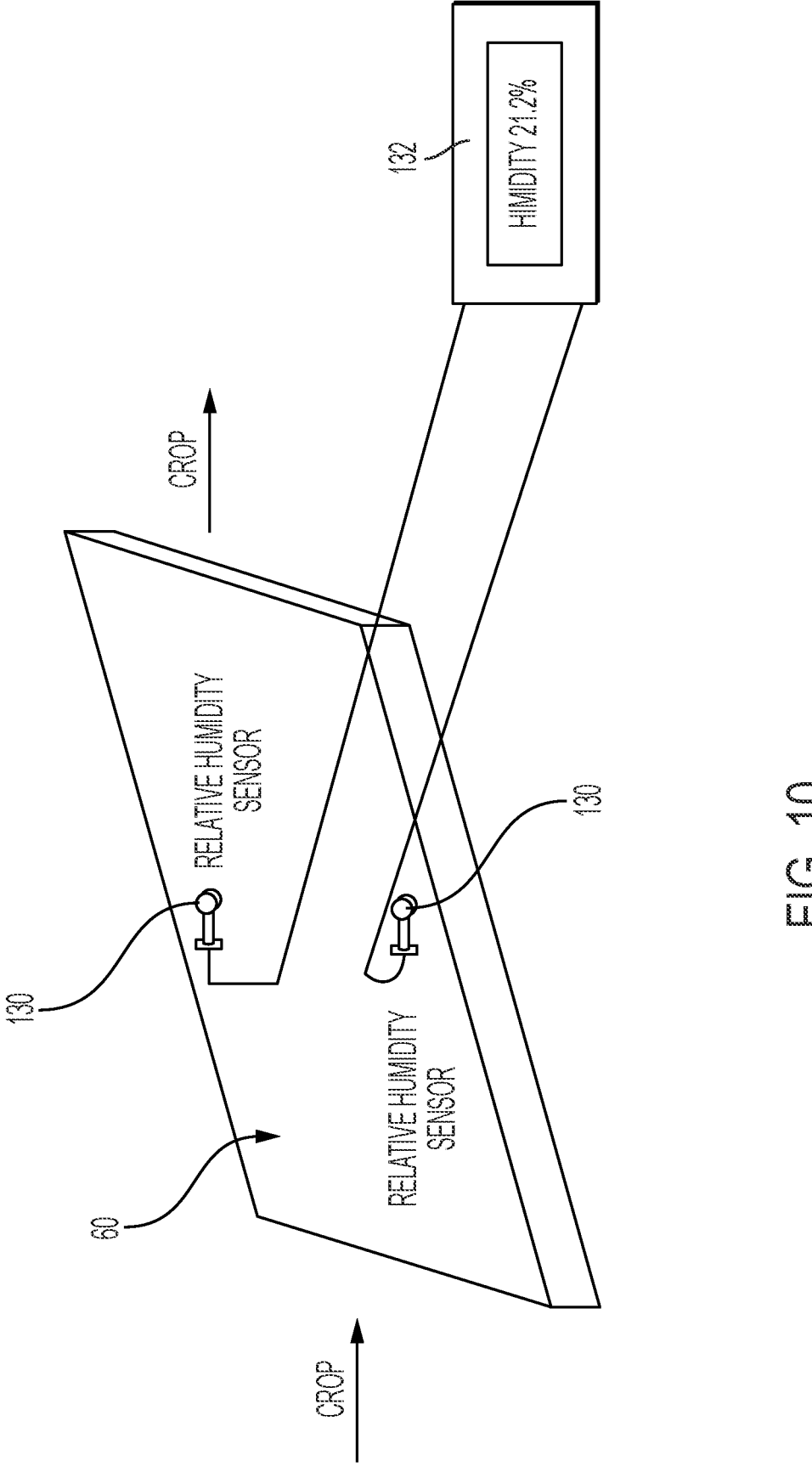
FIG. 10 illustrates another embodiment of a portion of a feeder house of an agricultural combine harvester.

In another embodiment as illustrated in FIG. 10, the top wall 60 supports two relative humidity sensors 130, which are the same or similar sensors as sensors 72 and 74, each of which provides relative humidity data within the feeder house 34 and outside the feeder house 34. The sensors measure relative humidity and temperature. The measured data is used by an advanced predictive algorithm to accurately measure crop moisture percentage. The predictive algorithm uses measure values of relative humidity and temperature as well as crop data such as crop type. The relative humidity data is transmitted from each of the relative humidity sensors 130 to a microcontroller 132. The relative humidity data received by the microcontroller 132 is used to determine a relative humidity of an interior space of the feeder house 34 as being 21.2 percent.

While exemplary embodiments incorporating the principles of the present disclosure have been described herein, the present disclosure is not limited to such embodiments. For instance, while a grain harvester has been described in detail, other crop harvesters, other types of combine harvesters harvester are included. Consequently, this application is intended to cover any variations, uses, or adaptations of the disclosure using its general principles. Further, this application is intended to cover such departures from the present disclosure as come within known or customary practice in the art to which this disclosure pertains.

What is claimed is:

1. A system for adjusting combine harvester machine settings based on a moisture content of a crop harvested by a combine harvester, the system comprising:

an enclosure including an inlet, an outlet, and a support located between the inlet and the outlet, the inlet configured to receive cut crop, the support positioned between an internal space of the enclosure and ambient air of an external environment located outside of the enclosure, a crop transfer device disposed within the enclosure configured to move cut crop through the enclosure from the inlet to the outlet;

a sensor assembly comprising a sensor housing having an internal support positioned between a top cover and a bottom cover of the sensor housing, the bottom cover connected to the support of the enclosure, wherein the sensor assembly further comprises a first sensor and a second sensor positioned within the sensor housing and coupled to opposing sides of the internal support, the first sensor configured to provide a first sensor output of one of or both of a relative humidity value and a temperature value of ambient air that is external to the enclosure, the second sensor configured to provide a second sensor output of one of or both of a relative humidity value and a temperature value of the internal environment; and a controller operatively connected to the sensor assembly, wherein the controller is configured to predict, using the first and second sensor outputs, the moisture content of the crop.

2. The system of claim 1 wherein the enclosure includes a top wall, a bottom wall, and at least one side wall, wherein one of the top wall, the bottom wall, or the at least one side wall supports the sensor assembly.

3. The system of claim 2 wherein the enclosure is a feeder house of the combine harvester.

4. The system of claim 2 wherein the sensor assembly includes a first aperture exposed to the external environment and a second aperture exposed to the internal space.

5. The system of claim 4 wherein the sensor assembly is adapted to calculate relative humidity based on predictive control implemented in a processor located on the sensor assembly.

6. The system of claim 5 wherein the top cover defines the first aperture and the bottom cover defines the second aperture.

7. The system of claim 6 wherein each of the first aperture and the second aperture include one of a mesh structure, a grate structure, or a perforated structure.

8. The system of claim 1 wherein the controller includes a processor and a memory, wherein the memory is configured to store program instructions and the processor is configured to execute the stored program instructions to determine one or more machine settings based on one or more outputs of the sensor assembly including:

a threshing speed of the combine harvester;

a concave clearance of a concave of the combine harvester;

a fan speed of a fan of the combine harvester; and a forward speed of the combine harvester.

9. The system of claim 8 further comprising a user interface operatively connected to the controller, wherein the user interface includes a display screen to display moisture content information of the crop based on one of or both of the relative humidity value and the temperature value.

10. The system of claim 9 wherein the processor is configured to execute the stored program instructions to provide adjustment indicators for adjusting one or more of the threshing speed, the concave clearance of the concave, speed of the fan, and the forward speed of the combine harvester when the relative humidity value exceeds a predetermined relative humidity value or the temperature value exceeds a predetermined temperature value.

11. The system of claim 9 wherein the processor is configured to execute the stored program instructions to automatically adjust one or more of the threshing speed, the concave clearance of the concave, speed of the fan, and the forward speed of the combine harvester when the relative humidity value exceeds a predetermined relative humidity value or the temperature value exceeds a predetermined temperature value.

12. A combine harvester for harvesting crop, the combine harvester comprising:

a header to cut crop;

a feeder house including an inlet, connected to the header, and an outlet, the feeder house defining an interior and an exterior located outside the feeder house;

a drum and a concave disposed within the feeder house, the concave disposed adjacently to the drum, a threshing unit operatively connected to the outlet of the feeder house;

a sensor assembly comprising a sensor housing connected to the feeder house, a first sensor, and a second sensor, the first sensor and the second sensor positioned within the sensor housing, the first sensor positioned to output an exterior relative humidity value or both of the exterior relative humidity value and an exterior temperature value for the exterior defined by the feeder house, the second sensor positioned to output an interior relative humidity value or both of the interior relative humidity value and an interior temperature value for the interior defined by the feeder house; and a controller operatively connected to the sensor assemblies assembly, wherein the controller receives the outputs from each of the first sensor and the second sensor.

13. The combine harvester of claim 12 wherein the sensor housing includes an internal support, a first aperture, and a second aperture, the first sensor being supported by the internal support of the sensor housing to be exposed to the exterior defined by the feeder house through the first aperture and the second sensor is supported by the internal support to be exposed to the interior defined by the feeder house through the second aperture.

14. The combine harvester of claim 13 wherein each of the first sensor and the second sensor includes a semiconductor polymer sensor.

15. The combine harvester of claim 13 wherein the sensor housing includes a sidewall, and a top cover and a bottom cover, each coupled to the sidewall, wherein the top cover defines the first aperture and the bottom cover defines the second aperture, and the internal support is located between the top cover and the bottom cover.

16. The combine harvester of claim 15 wherein each of the first aperture and the second aperture include one of a mesh structure, a grate structure, or a perforated structure.

17. The combine harvester of claim 12 wherein the controller includes a processer and a memory, wherein the memory is configured to store program instructions and the processor is configured to execute the stored program instructions to adjust one or more of:

a threshing speed of the combine harvester;

a concave clearance of a concave of the combine harvester;

a fan speed of a fan of the combine harvester; and a forward speed of the combine harvester.

18. A method of modifying the operation of a combine harvester while harvesting crop from a field comprising:

threshing cut crop as the combine harvester moves through the field;

identifying, from an information outputted by a first sensor and a second sensor housed within a sensor housing that is mounted to a feeder house of the combine harvester, a relative humidity value or both of a relative humidity value and a temperature value in both an interior and an exterior that are defined by the feeder house;

adjusting one or more of a plurality of machine operations including: i) a threshing speed of the combine harvester; ii) a concave clearance of a concave of the combine harvester; iii) a fan speed of a fan of the combine harvester; and iv) a forward speed of the combine harvester based on the determined relative humidity value or both of the relative humidity value and temperature value in the feeder house.

19. The method of claim 18 wherein the adjusting step includes adjusting one or more of the plurality of machine settings in response to one of: i) a user input received from a user interface or ii) automatically based on an instruction from a controller processor.

20. The method of claim 19 wherein the identifying step includes identifying the relative humidity value or both of the relative humidity value and temperature value in the interior and the exterior of the feeder house with the first sensor directed to the exterior that is defined by the feeder house and the second sensor directed to the interior that is defined by the feeder house.

* * * * *